(12) United States Patent
Chen et al.

(10) Patent No.: US 7,337,759 B1
(45) Date of Patent: Mar. 4, 2008

(54) ENGINE

(76) Inventors: Yung-ching Chen, #6, Chang Ping East 6th Road, Hsien Hsi Shang, Changhua (TW); Chih-chieh Chen, #6, Chang Ping East 6th Road, Hsien Hsi Shang, Changhua (TW)

(*) Notice: Subject to any disclaimer, the term of this patent is extended or adjusted under 35 U.S.C. 154(b) by 0 days.

(21) Appl. No.: 11/543,111

(22) Filed: Oct. 5, 2006

(51) Int. Cl.
*F02B 75/32* (2006.01)
(52) U.S. Cl. .................................. 123/197.4
(58) Field of Classification Search ............. 123/197.4, 123/197.1, 65 R, 58.5, 58.6, 65 S
See application file for complete search history.

(56) References Cited

U.S. PATENT DOCUMENTS 1,413,541 A * 4/1922 Reed ........................ 123/77
6,662,764 B2 * 12/2003 Chen et al. ............... 123/65 R

* cited by examiner

*Primary Examiner*—Stephen K. Cronin
*Assistant Examiner*—Hyder Ali
(74) *Attorney, Agent, or Firm*—Rabin & Berdo, P.C.

(57) ABSTRACT

The invention involves an engine that the cylinder block contains a coupled piston formed by a main piston, an external piston. The external piston is sleeved outside of the main piston and uses the rods on the two sides to connect to the heart-shape groove on the two sides of the crankshaft inside the crankcase at the bottom of the cylinder block. It moves with the main piston in an upward stroke and in a downward stroke. It forms a direct fuel injection device in the cylinder without carburetor. It does not need to add lubricants in the fuels. Besides, the engine has increased compression ratio.

9 Claims, 8 Drawing Sheets

ENGINE

BACKGROUND OF THE INVENTION

1. Field of the Invention

The invention is related to the structure of a two-stroke internal combustion engine. Especially, it involves a type of engine that converts the instant power of fuel into cyclic linear movement of an external piston.

2. Description of the Prior Art

Current internal combustion engines (engine) are mainly two-stroke or four-stroke. Please refer to FIG. 1 for the structure for a common two-stroke engine. Its cylinder block 10 has an air intake 11 and an air exhaust 12 on two opposite sides. A piston 13 has a sealing piston ring 14 inside the cylinder block 10. One end of a connecting rod 15 connects to a piston pin 16 inside the piston 13. The other end of the connecting rod 15 connects to a crankshaft 18 inside a crankcase 17 at the bottom of a cylinder block 10. When the piston 13 is in an upward stroke at the top of cylinder block 10 to compress the mixed fuels, a spark plug 19 ignites the fuels to explode and force the piston 13 in a downward stroke. Then through the crankshaft 18, the power is output. When the piston 13 is below the air exhaust 12 in a downward stroke, the combustion waste gases are exhausted. Upon exhausting the waste gases, the air exhaust 12 experiences a Venturi effect that builds up pressure in the crankcase, so the pressure in the top of the cylinder block 10 becomes negative. The air intake 11 (with check valve) sucks in mixed fuel gases. At this moment, the piston 13 uses the rotational power from the connecting rod 15 and the crankshaft 18 to generate an upward stroke and compress the mixed fuel gases again and ignite to explode. From the description above, it is known that the two-stroke engine has advantages in simple structure, low power loss and high power output. Since the piston 13 passes by the air intake 11 and the air exhaust 12 on two opposite sides of the cylinder block 10 in an upward stroke and a downward stroke, the crankcase 17 cannot store engine oils inside. But because mechanical movement needs lubrication, the two-stroke engine needs lubricants in its fuels. Thus, combustion causes lubricant film formations and the combustion is apparently incomplete. This leads to emission of polluting waste gases that cause environmental issues. The objective of the invention is to provide for a two-stroke engine to minimize pollution from emission of waste gases and increase its power output.

SUMMARY OF THE INVENTION

Therefore, the main objective of the invention is to provide a two-stroke engine that places an external piston on the main piston. The external piston uses two side connecting rods to connect to the two sides of the crankshaft in a heart-shape groove and is able to move with the main piston in an upward stroke and a downward stroke, so the explosive power from combustion is converted to cyclic linear motion. This is to replace the complicated air valve structure in a four-stroke engine. The invention also adds blocking rings to the skirt section of the external piston and the main piston. This design and the pre-compression single-stream airway inside the crankcase can provide lubrication as four-stroke engine does and remove the restriction that two-stroke engine has to add lubricants to its fuels.

Another objective for the invention is for the external piston to close the air intake valve and the air exhaust valve early and block the leaking of the mixed fuel gases in the cylinder by angular variation of the heart-shape grooves on the two opposite sides of the crankshaft, and also to increase gas intake capacity for the cylinder and the compression ratio to add power.

Another objective for the invention is to provide an engine with an oil supply system that uses the oil pump driven by the heart-shape grooves on the two sides of the crankshaft to lubricate mechanical parts and replace carburetors. It pumps out fixed amount of oils in standard mixing ratio and prevents backflow of oils by a check valve. Through one-way pressure-regulating valve, the fuel enters in one way. Fuel supply is adjustable and a stable amount of fuel is directly injected to the cylinder to overcome the shortcoming of traditional carburetors and electronic fuel injectors.

Another objective of the invention is to provide an engine that the 1st stage cylinder bore of the external piston and cylinder block has waving edges, so when the external piston and the cylinder block contact each other, there is waving contact surface and the main piston and the external piston move at the same time. The piston ring of the main piston can enter or leave smoothly the chamber of the external piston without jamming up the groove.

To realize the above objective, the invention provides an engine that its cylinder block has coupled piston comprising a main piston and an external piston. The mentioned external piston encloses the main piston and uses two sides connecting rods to connect to the two sides of the crankshaft in a heart-shape groove inside the crankcase at the bottom of the cylinder block, so it moves along with the main piston in an upward stroke and a downward stroke.

It is preferred that the skirt section for the main piston or the external piston for the coupled piston has blocking rings to prevent lubricants from leaking through air intake and air exhaust.

It is more preferred that the heart-shape grooves at the two sides of the crankshaft driving the external piston in an upward stroke and a downward stroke are formed by connection of large and small circular grooves.

It is also more preferred that the heart-shape grooves at the two sides of the crankshaft are concave, convex or combination of both as toothed wheels.

It is also more preferred that the cylinder bore is two sections in the cylinder block, and has two different inner diameters.

It is also more preferred that that the crankcase at the bottom of the cylinder block passes to a single-stream independent airway and controls the direction of gas flow through the airway.

It is also more preferred that the gases inside the crankcase at the bottom of the cylinder block enter the cylinder through a single-stream independent airway or leave the crankcase before re-entering the cylinder.

It is also more preferred that the cylinder has a direct fuel injection system composed of an oil pump, a check valve and a regulating valve. The power for oil supply system is generated by the rotation of heart-shape grooves on two sides of the crankshaft inside the crankcase at the bottom of the cylinder block.

It is also more preferred that the contact surface of the external piston and the first section of the cylinder are waving.

DETAILED DESCRIPTION OF THE PREFERRED EMBODIMENT

Figure 1:
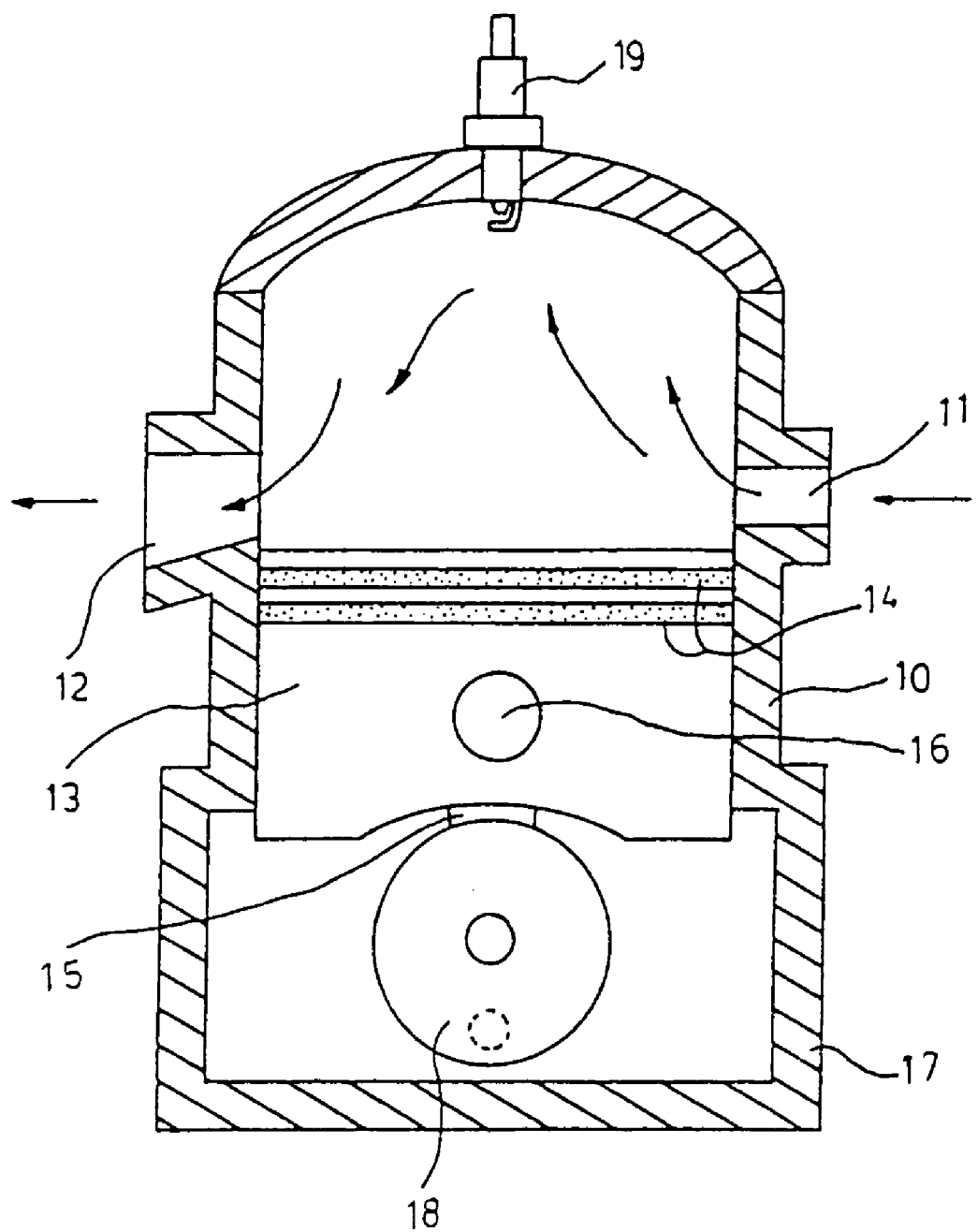
FIG. 1 is an illustration for the structure of a common two-stroke engine.
Figure 2:
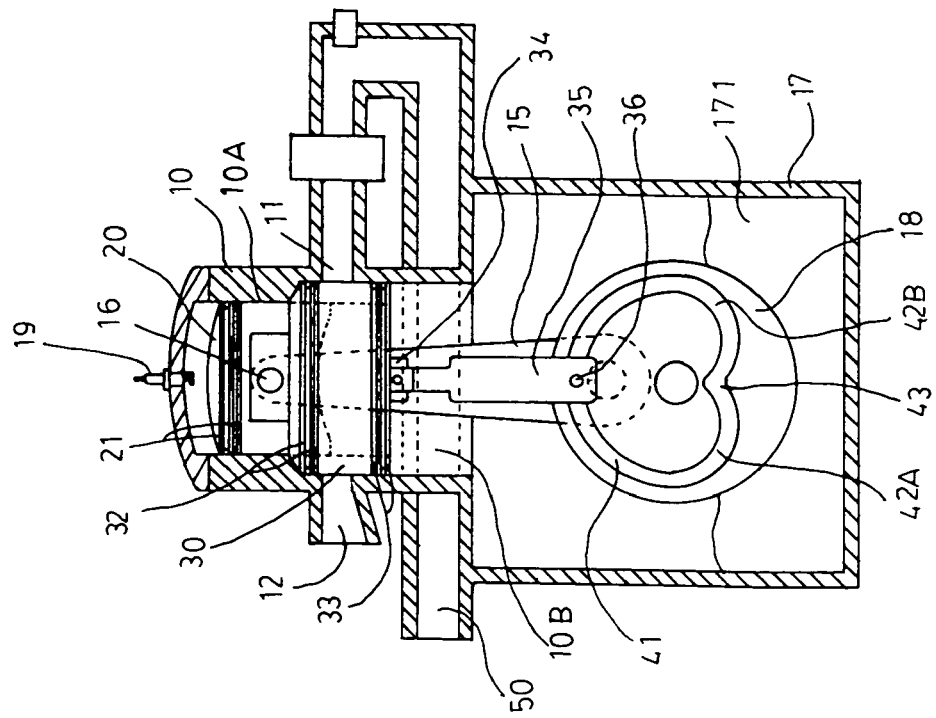
FIG. 2 is an illustration for the structure of the engine in the invention (compression and ignition).
Figure 3:
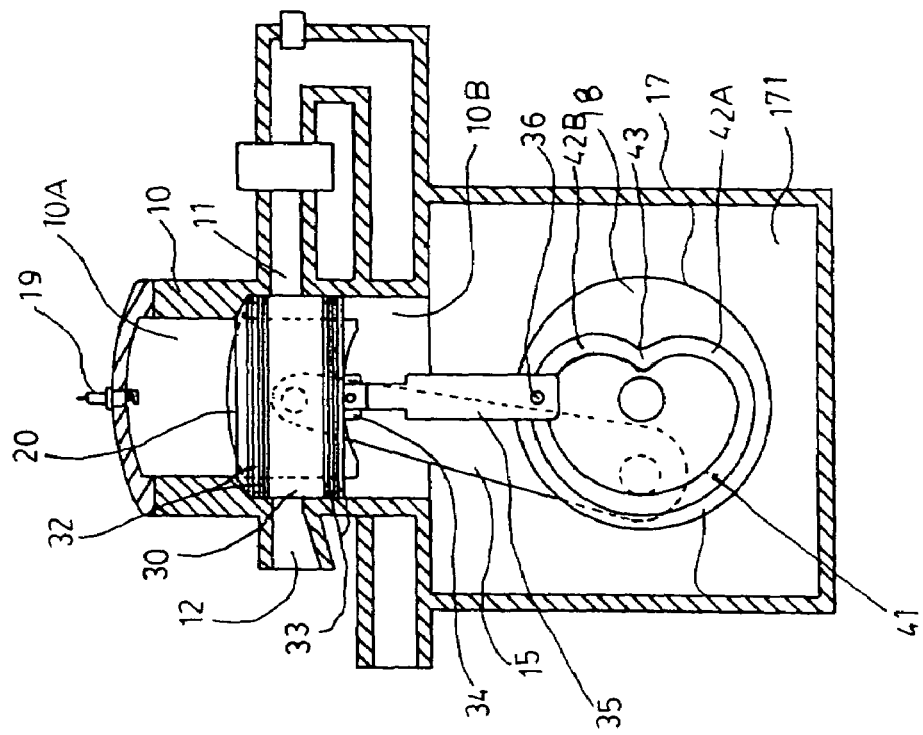
FIG. 3 is an illustration for the structure of the engine in the invention (explosion, main piston in a downward stroke).
Figure 4:
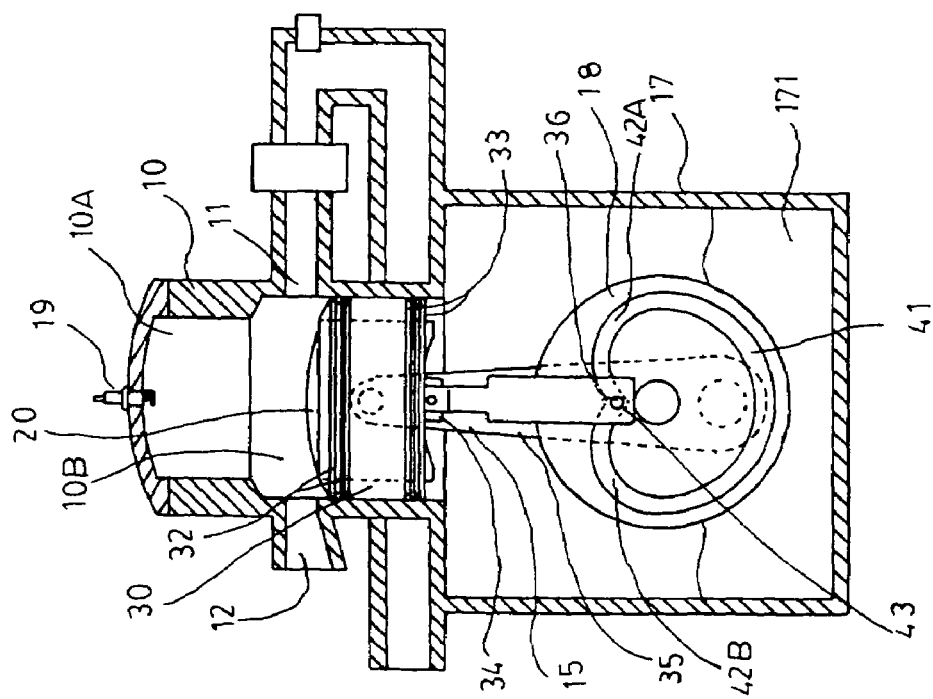
FIG. 4 is an illustration for the structure of the engine in the invention (exhaust and intake).
Figure 5:
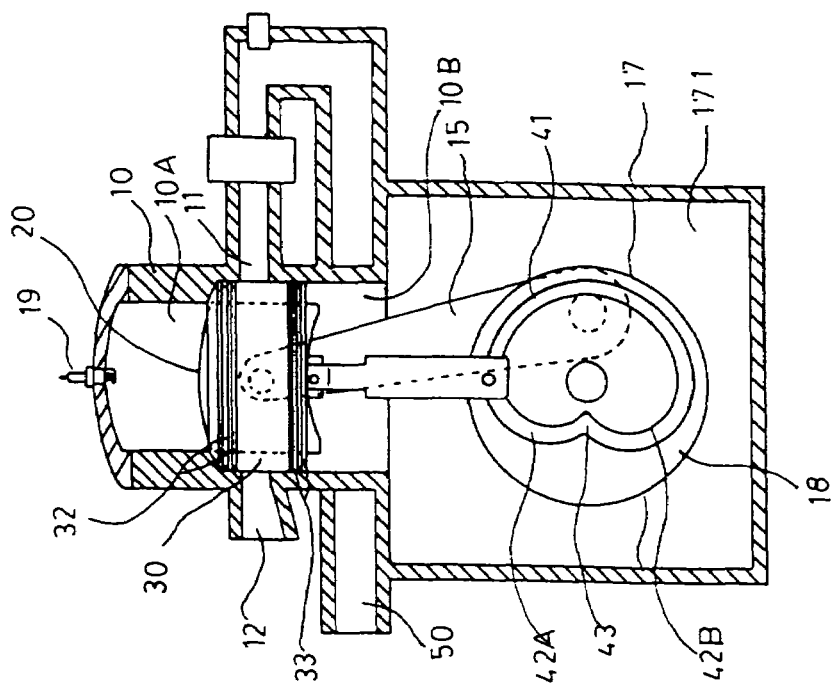
FIG. 5 is an illustration for the structure of the engine in the invention (external piston is closing air intake and air exhaust while the main piston is in an upward stroke before compression).
Figure 6:
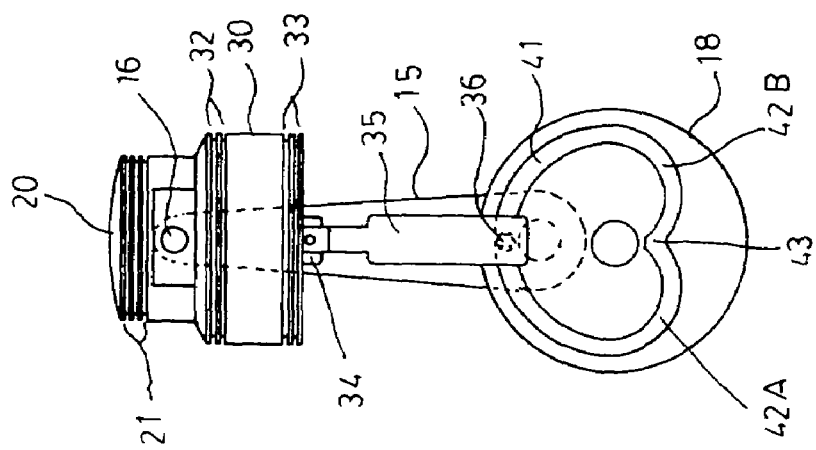
FIG. 6 is a side view for the connection of the coupled piston and the crankshaft in the invention.
Figure 7:
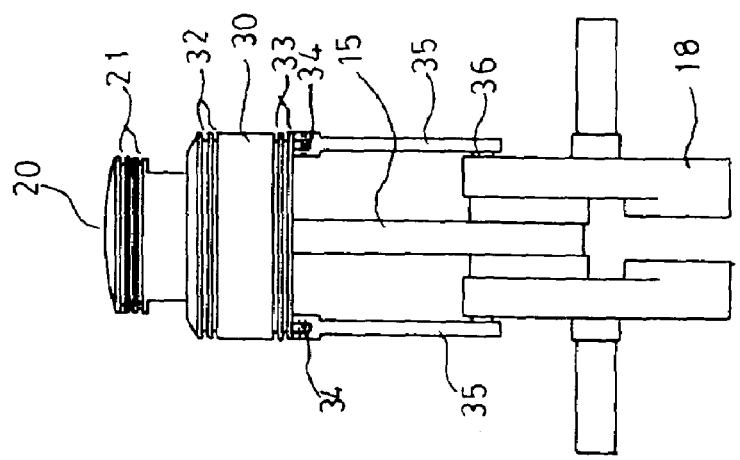
FIG. 7 is a front view for the connection of the coupled piston and the crankshaft in the invention.
Figure 8:
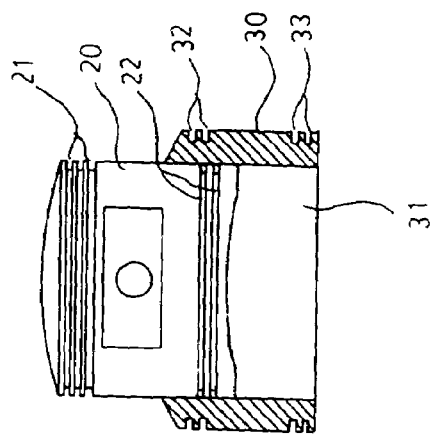
FIG. 8 is a cross-section diagram for the coupled piston in the invention.

To further explain the objective, features and benefits of the invention, a preferred embodiment is described as follows:

Please refer to FIG. 2 to FIG. 8. The structure for the engine in the invention mainly uses a coupled piston structure consisting of a main piston 20 and an external piston 30 inside a cylinder block 10. When the coupled piston moves inside the cylinder block 10 in an upward stroke and a downward stroke, the external piston 30 can open or close the air intake 11 and the air exhaust 12 on the two opposite sides of the cylinder block 10. This prevents the lubricants 171 stored inside the crankcase 17 from leaking out. Thus, the invention utilizes the lubrication concept of four-stroke engine to overcome the restriction of a two-stroke engine of having to add lubricants in the fuels, to improve the emission of waste gases. The features for the invention are as in FIG. 8 that shows the main piston 20 has a sealing piston ring 21 at top and a sealing blocking ring 22 at a skirt; the external piston 30 has a chamber 31 passing through its interior, a sealing piston ring 32 at top, a sealing blocking ring 33 at a skirt; the main piston 20 is able to move up and down inside the chamber 31 of the external piston 30; one end of a connecting rod 15 connects to a piston pin 16 and also links to the main piston 20 while the other end connects to the crankshaft 18 inside the crankcase 17 at the bottom of the cylinder block 10; a rod seat 34 at the two opposite sides of the bottom end of the skirt of the external piston 30 is for connection of one end of the rod 35 while the other end connects to a guide pulley 36, so the rod 35 uses the guide pulley 36 to lie against the heart-shaped grooves on the two sides of the crankshaft 18 and is thus driven to move the external piston 30 in a upward stroke and a downward stroke; the heart-shaped groove is ring shaped grooves on the two sides of the crankshaft 18, concave or convex or a combination of both as toothed wheel, with one half as large circular groove 41 coaxial with the crankshaft 18 and the other half forms two small circular groove 42A and 42B non-coaxial with the crankshaft 18; a groove low point 43 is formed and near the center of crankshaft 18 between openings of the two small circular grooves 42A and 42B; the interior of cylinder block 10 has two sections, the 1 st stage cylinder bore 10A equivalent to the outside diameter of the main piston 20, the 2nd stage cylinder bore 10B equivalent to the outside diameter of the external piston 30, while the air intake 11 and the air exhaust 12 on the two opposite sides of the cylinder block 10 are located on the 2nd stage cylinder bore 10B; as shown in FIG. 2, FIG. 6 and FIG. 7 at this location the crankshaft 18 uses the connecting rod 15 to push the main piston 20 up to inside the 1st stage cylinder bore 10A of the cylinder block 10, and the main piston 20 uses its top piston ring 21 to seal the compressed mixed fuel gases, and the heart-shape grooves on the two sides of the crankshaft 18 use the large circular groove 41 to push against the guide pulley 36 of the rod 35 and allow the external piston 30 to remain at the top of the 2nd stage cylinder bore 10B of the cylinder block 10, and the piston ring 32 and the blocking ring 33 at the top and the skirt are around the position of the air intake and the air exhaust 11, 12 to stop the lubricants inside the crankcase 17 from leaking through the air intake and the air exhaust 11, 12; as shown in FIG. 3 at this position, the spark plug 19 ignites the compressed mixed fuel gases and pushes the main piston 20 in a downward stroke into the chamber 31 of the external piston 30, and the downward main piston 20 uses the connecting rod 15 to push the crankshaft 18 counterclockwise 90 degrees, and the rods 35 at the two sides of the external piston 30 still have their guide pulley 36 inside the heart-shape large circular groove 41, so the rods 35 do not move with the main piston 20 and are still at the position to seal the air intake and the air exhaust 11, 12; as shown in FIG. 4 at this position the main piston 20 continues its downward stroke and uses the connecting rod 15 to push the crankshaft 18 counterclockwise to 180 degrees, and at the same time the guide pulley 36 on the rods 35 on the two sides of the external piston 30 enters from one small circular groove 42B into the heart-shape groove low point 43, and the rod 35 can pull the external piston 30 and moves together with the main piston 20 downward to open the air intake and the air exhaust 11, 12; as shown in FIG. 5 at this position the crankshaft 18 continues to rotate counterclockwise to about 270 degrees and pushes the main piston 20 and the external piston 30 together upward to the top point of the 2nd stage cylinder bore 10B of the cylinder block 10, and the external piston 30 seals the air intake and the air exhaust 11, 12 again until it gets back to the position shown in FIG. 2, and the crankshaft 18 completes a full cycle (360 degrees) and drives the main piston 20 upward again to compress the mixed fuel gases; in summary, the coupled piston composed of the main piston 20 and the external piston 30 is to prevent the leaking of lubricants 171 inside the crankcase 17 from leaking through the air intake and the air exhaust 11, 12, and a four-stroke engine concept is used to solve the emission pollution issue for two-stroke engine that had to add lubricants to the fuels; further, through the angular variation of the large circular grooves 41 on the two sides of the crankshaft 18 and the two small circular grooves 42A, 42B, the external piston 30 can close out in an early time the air intake and air exhaust 11, 12 on the two opposite sides of the cylinder block 10 to prevent the leaking of the mixed fuel gases inside the cylinder block 10, and the external piston 30 can also increase air intake to raise up the compression ratio and the power output as well.

Figure 10:
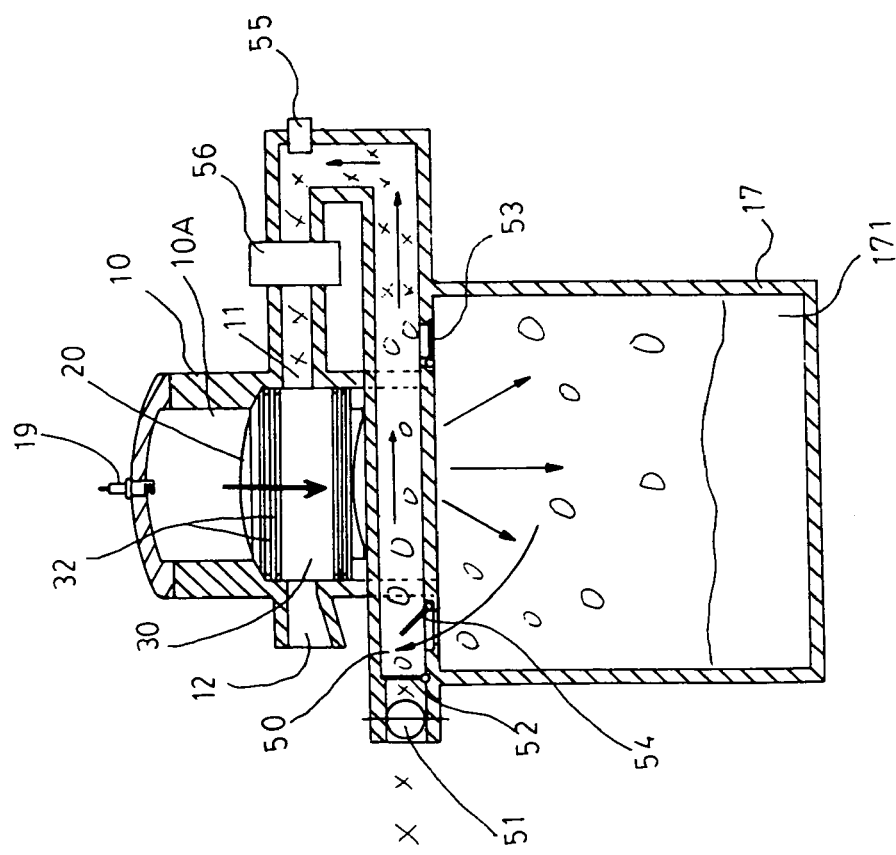
FIG. 10 is an illustration for gas flow in the different sections of the single-way independent airway for the invention.
Figure 9:
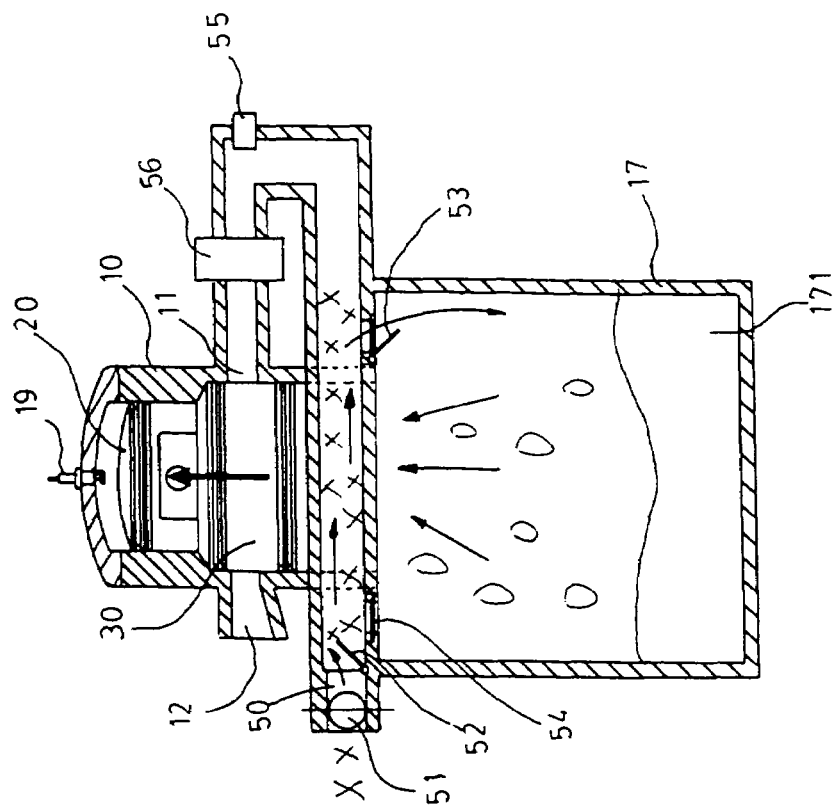
FIG. 9 is an illustration for gas flow in the different sections of the single-way independent airway for the invention.

Please refer to FIG. 9 and FIG. 10. They are the illustrations for gas flow in the different sections of the single-way independent airway for the invention. The inlet of the single-flow independent airway 50 has throttle valve 51 and the first check valve 52, and the second check valve 53 on the way to the crankcase 17, the third check valve 54 on the same way to the airway 50, and the end of the independent airway 50 connects to the air intake 11 for the cylinder block 10, and a fuel injector 55 or a carburetor 56 is in the middle; thus, the independent airway 50 capacity is determined by the air intake volume due to the upward stroke of the main piston 20 and the external piston 30 inside the cylinder block 10 to the top point of the crankcase 17, as shown in FIG. 9. When the main piston 20 and the external piston 30 move upward to the top point (compression, ignition), an equal amount of air intake from the crankcase 17 lowers the air pressure inside the crankcase 17 and opens up the second check valve 53 to allow outside air going to the airway 50 (indicated by X); as shown in FIG. 10, when the main piston 20 and the external piston 30 move downward to the bottom point (explosion, exhaust) of the cylinder block 10, they compress the air inside the crankcase 17 and close the first check valve 52 and the second check valve 53, and open the third check valve 54, and press the mixed lubricated fuel gases (indicated by 0) inside the crankcase 17 into the independent airway 50 and push the outside air (indicated by X) already inside the independent airway 50 through the fuel injector 55 or the carburetor 56 and the air intake 11 to the cylinder block 10; in this way, the invention uses the first check valve 52, the second check valve 53 and the third check valve 54 to control the single-way flow in the airway, and allow the outside air (indicated by X) and the crankcase 17 fuel gases (indicated by O) to enter in sequence, and as a result the fuel gases (indicated by O) inside the crankcase 17 always circulate in the independent airway 50 and the crankcase 17, and after the outside air (indicated by X) enters the independent airway 50, it does not enter the crankcase 17, instead, is pushed through the fuel injector 55 or the carburetor 56 and the air intake 11 to the inside of the cylinder block 10.

Figure 11:
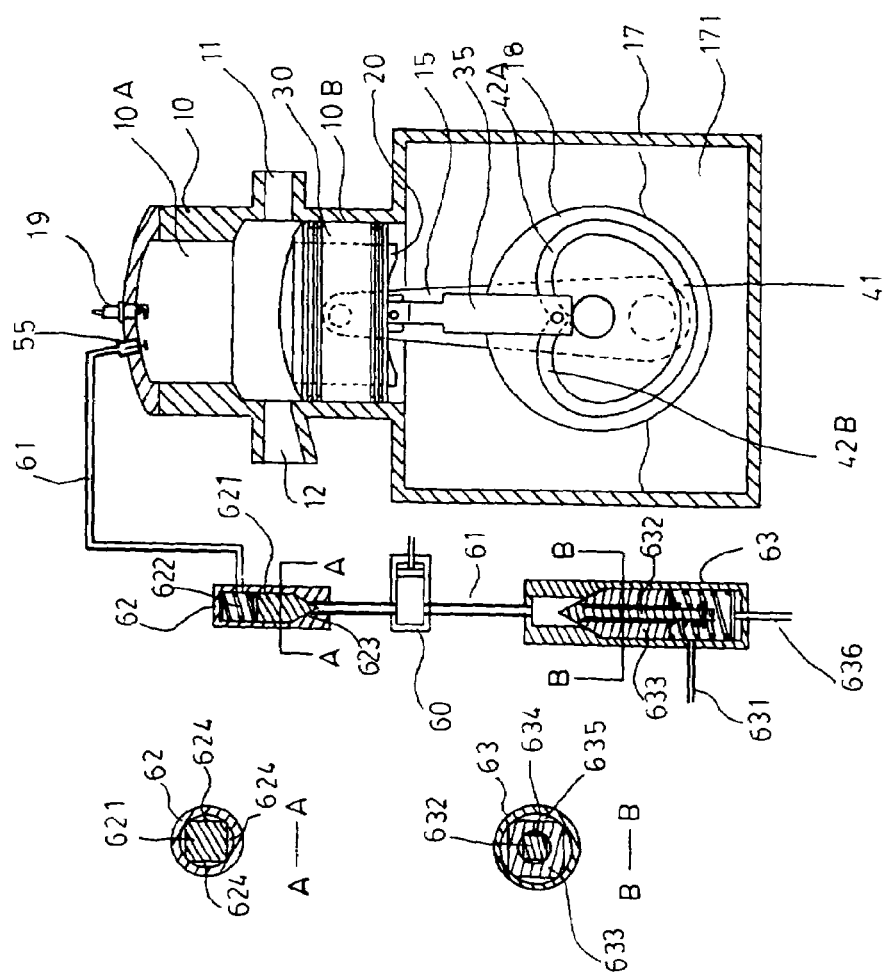
FIG. 11 is an illustration for the direct fuel injection system for the cylinder in the invention.

Please refer to FIG. 11 for the coupled piston and the direct fuel injection system in the invention. The oil supply system consists of an oil pump 60, a check valve 62, one-way regulating valve 63 and the fuel lines 61 in the middle. The oil pump 60 is driven by the rotation of the heart-shape grooves on the two sides of the crankshaft 18 and the standard mixed fuel is sucked through fuel feed lines 631 and the one-way regulating valve 63 into the oil pump 60. After pressurization of the oil pump 60, the fuel is injected by the check valve 62 and the fuel injector 55 into the cylinder block 10. The valve body 621 of the check valve 62 is subject to push by the rear spring 622 to close the valve port 623 and stop the backflow of the fuel inside the fuel injector 55. Please refer to A-A Figure. The four sides of the valve body 621 are four flat surfaces. When the oil pump 60 pumps a certain quantity of fuel to push the valve body 621 backward to open the valve port 623, the fuel can pass through the clearance 624 among four flat sides and flow to the fuel injector 55 through the check valve 62; the one-way regulating valve 63 has a regulating screw 636 in the front end, a fuel feed line 631 on its side, a fuel line 61 connecting to an oil pump 60 in the back, and a valve rod 632 penetrating inside the valve body 633. The valve rod 632 and the valve body 633 have four flat surfaces on four sides. Pressurized gasoline through the fuel feed line 631 enters the one-way regulating valve 63 and flows between clearance 634 between flat surfaces on the four sides of the valve rod 632 to push the valve rod 632 forward and open, so the fuel flows into the fuel line 61 in one way. When the oil pump 60 pumps the fuel in the fuel line 61 into the check valve 62, if pressure is built up, it can push back the valve body 623 of the one-way regulating valve 63 and the valve rod 632 backward. This allows the pressurized fuel to flow back to the inside of the one-way regulating valve 63 through the flat clearance 635 on the four sides of the valve body 633, then flow back to the fuel tank through the fuel feed line 631. Thus, it enables the fuel injector 55 injects the fuels to the cylinder block 10 stably and directly.

Figure 12:
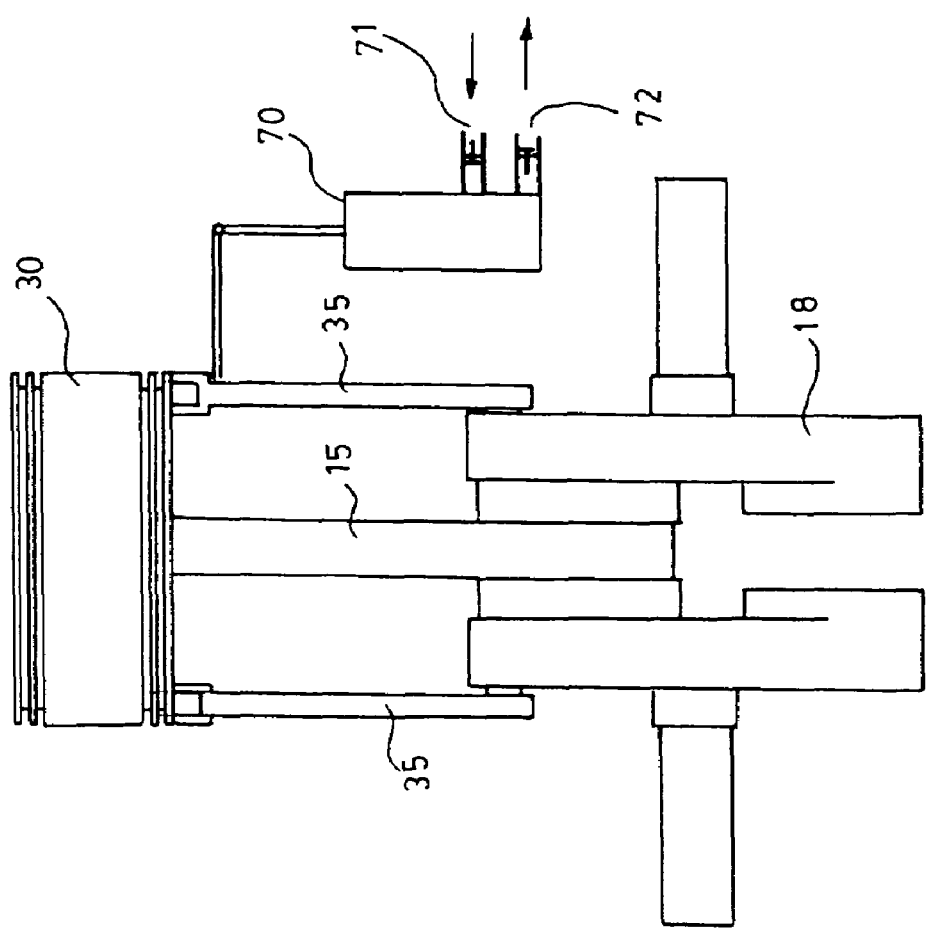
FIG. 12 is an illustration for the oil pump system of the lubrication device in the invention.

Please refer to FIG. 12. The invention uses a coupled piston that moves simultaneously and is added a lubricating oil pump. The oil pump system includes an oil pump 70 and its fuel feeding check valve port 71, fuel discharge check valve port 72. The oil pump 70 is driven by the rotating heart-shape groove on the two sides of the crankshaft 18 or the rod 35 of the external piston 30.

Figure 14:
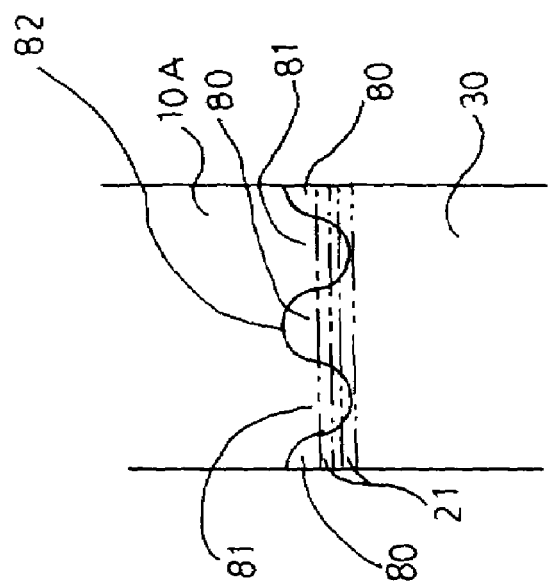
FIG. 14 is an illustration for the operation of the joint in FIG. 13 and the piston ring of the main piston.
Figure 13:
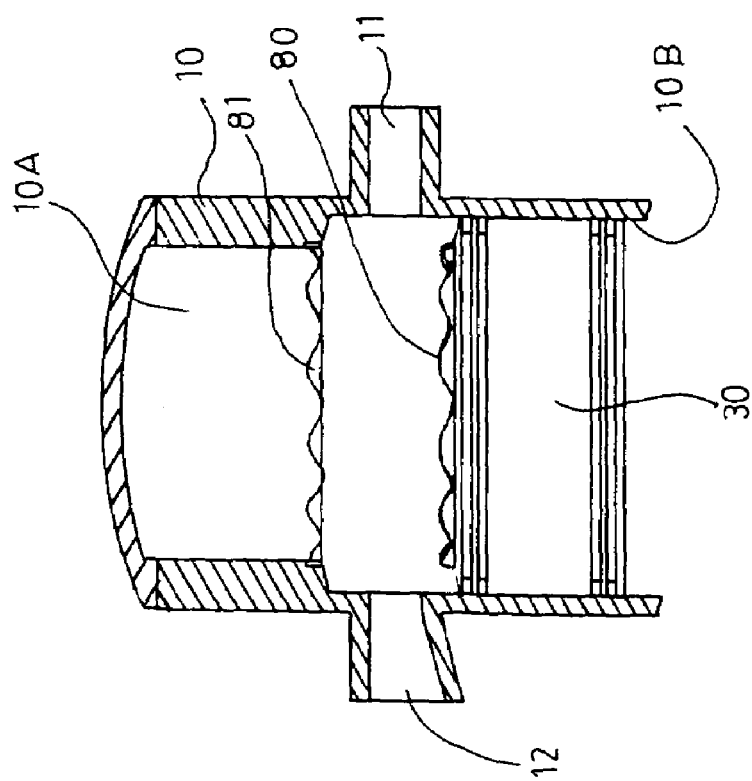
FIG. 13 is an illustration for the structure of the joint between the external piston and the cylinder block in the invention.

Please refer to FIG. 13 and FIG. 14 for the structure of the joint of the external piston and the cylinder block and its relation with the piston ring of the main piston. The top of the chamber 31 for the external piston 30 has waving flange 80. The bottom of the 1 st stage cylinder bore 10A for the cylinder block 10 has corresponding waving flange 81. When the external piston 30 is located at the top of the $2^{nd}$ stage cylinder bore 10B for the cylinder block 10. The waving flange 80 at the top of the chamber 31 is inserted into the waving flange 81 at the bottom of the 1st stage cylinder bore 10A. In this way, it forms waving joint (as shown in FIG. 14). When the main piston 20 is in the same upward and downward strokes with the external piston 30 in the chamber 31, when the piston ring 21 passes the interface of the external piston 30 and the 1st stage cylinder bore 10A, it passes smoothly, so the piston ring 21 for the main piston 20 will not be stuck in the groove.

In summary, the invention improves the emission for a two-stroke engine without the complicated structure of valves in a four-stroke engine, and also increases air intake for the cylinder and its compression ratio to boost the power output. Besides, it also has the advantage of using the direct fuel injection system without carburetor.

Description of Main Components

| | |
|---|---|
| 10 | cylinder block |
| 10A | 1st stage cylinder bore |
| 10B | 2nd stage cylinder bore |
| 11 | air intake |
| 12 | air exhaust |
| 13 | piston |
| 14 | piston ring |
| 15 | Connecting rod |
| 16 | piston pin |
| 17 | crankcase |
| 171 | Lubricating oil |
| 18 | crankshaft pin |
| 19 | spark plug |
| 20 | Main piston |
| 21 | piston ring |
| 22 | blocking ring |
| 30 | External piston |
| 31 | chamber |
| 32 | piston ring |
| 33 | Blocking ring |
| 34 | rod seat |
| 35 | rod |

| | |
|---|---|
| 36 | guide pulley |
| 41 | large circular groove |
| 42A | small circular groove |
| 42B | small circular groove |
| 43 | groove low point |
| 50 | One-way independent airway |
| 51 | throttle valve |
| 52 | 1st check valve |
| 53 | 2nd check valve |
| 54 | 3rd check valve |
| 55 | fuel injector nozzle |
| 56 | carburetor |
| 60 | oil pump |
| 61 | fuel line |
| 62 | check valve |
| 621 | valve body |
| 622 | compression spring |
| 623 | valve port |
| 624 | clearance |
| 63 | one-way regulating valve tuning check valve |
| 631 | fuel feeding intake oil hose |
| 632 | valve rod |
| 633 | valve body |
| 634 | valve rod clearance |
| 635 | valve body clearance |
| 636 | regulating screw |
| 70 | oil pump |
| 71 | Fuel feeding check valve port |
| 72 | Fuel discharge check valve port |
| 80 | waving convex flange |
| 81 | waving concave flange |
| 82 | Waving joint |

What is claimed is:

1. An engine, comprising:
a cylinder block;
a main piston and an external piston forming a coupled piston, and being contained in said cylinder block, the external piston being sleeved outside of the main piston;
a crankshaft having heart-shaped grooves on two sides thereof and being at a bottom of the cylinder block; and two side rods that connect the external piston to the heart-shaped grooves, the external piston moving with the main piston in an upward stroke and a downward stroke.

2. The engine as described in claim 1, wherein the main piston and the external piston each have a skirt, and wherein the skirt for the main piston or the skirt for the external piston has a blocking ring to prevent a leaking of lubricants through an air intake and an air exhaust.

3. The engine as described in claim 1, wherein each heart-shaped groove is comprised of a large circular groove and a small circular groove.

4. The engine as described in claim 1, wherein the heart-shaped grooves are concave, convex or a combination of both.

5. The engine as described in claim 1, wherein the cylinder block includes a cylinder bore comprised of two sections having two different inner diameters.

6. The engine as described in claim 1, further comprising a crankcase at the bottom of the cylinder block connected to a one-way independent airway to control a gas flow direction.

7. The engine as described in claim 1, further comprising a crankcase at the bottom of the cylinder block, wherein gases in the crankcase flow to the cylinder block through a one-way independent airway or leave the crankcase and re-enter the cylinder block.

8. The engine as described in claim 1, further comprising a direct fuel injection system in the cylinder block, and being comprised of an oil pump, a check valve, and a one-way regulating valve, power for driving the oil pump coming from a rotation of the heart-shaped grooves.

9. The engine as described in claim 1, wherein the cylinder block includes a cylinder bore comprised of first and second stages, and wherein a joint surface for the external piston and the first stage cylinder bore is wavy.

* * * * *